United States Patent
Barth

(10) Patent No.: US 7,138,672 B2
(45) Date of Patent: Nov. 21, 2006

(54) APPARATUS AND METHOD FOR MAKING A TENSILE DIAPHRAGM WITH AN INSERT

(75) Inventor: Phillip W. Barth, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/670,551

(22) Filed: Sep. 25, 2003

(65) Prior Publication Data

US 2005/0070042 A1    Mar. 31, 2005

(51) Int. Cl.
*H01L 23/58* (2006.01)

(52) U.S. Cl. .............. 257/253; 257/419; 257/619; 977/733

(58) Field of Classification Search ............... 257/253, 257/414, 419, 618, 619; 977/DIG. 1, 733
See application file for complete search history.

(56) References Cited

U.S. PATENT DOCUMENTS 5,393,401 A * 2/1995 Knoll ................... 204/403.06
6,686,299 B1 * 2/2004 Montemagno et al. ...... 438/800

FOREIGN PATENT DOCUMENTS

WO    WO 01/81896    11/2001
WO    WO 01/81908    11/2001

OTHER PUBLICATIONS

Kasianowicz et al., "Characterization of Individual Polynucleotide Molecules Using a Membrane Channel", Proc. Natl. Acad. Sci USA, vol. 93, pp. 13770-13773, Nov. 1996.
Li et al., "Ion-Beam Sculpting At Nanometre Length Scales", Nature, vol. 412, Jul. 12, 2001, pp. 166-169.

* cited by examiner

*Primary Examiner*—N. Drew Richards

(57) ABSTRACT

An apparatus and method for making a tensile diaphragm with an insert region of a material dissimilar to the diaphragm, the insert region being suitable for the fabrication of a nanopore.

24 Claims, 5 Drawing Sheets

APPARATUS AND METHOD FOR MAKING A TENSILE DIAPHRAGM WITH AN INSERT

TECHNICAL FIELD

The invention relates generally to the field of nanopores and more particularly to an apparatus and method for making a tensile diaphragm with an insert region of a material dissimilar to the diaphragm, the insert region being suitable for the fabrication of a nanopore.

BACKGROUND

Manipulating matter at the nanometer scale is important for many electronic, chemical and biological advances (See Li et al., "Ion beam sculpting at nanometer length scales", *Nature*, 412: 166–169, 2001). These pores have also been effective in localizing molecular-scale electrical junctions and switches (See Li et al., "Ion beam sculpting at nanometer length scales", *Nature*, 412: 166–169, 2001).

Artificial nanopores have been fabricated by a variety of research groups with a number of materials. Generally, the approach is to fabricate these nanopores in a solid-state material or a thin freestanding diaphragm of material supported on a frame of thick silicon. One material that has been used is silicon nitride. Silicon nitride diaphragms exhibit high burst pressures due to high yield strength of the silicon nitride material and due to moderate-to-high tensile stresses built into the diaphragm material that keeps the diaphragm uniformly flat. It is desirable to use other materials such as polymers, metals, and self-assembled monloayers for nanopore fabrication, but most materials are weaker than silicon nitride and may exhibit compressive stress. It, therefore, is desirable to have a diaphragm structure with an insert region of a dissimilar material that is capable of being used for nanopore fabrication, wherein neither the diaphragm nor the insert region suffer from the problems of buckling before or after fabrication. It is also desirable to provide a diaphragm structure that exhibits high burst pressures and does not wrinkle. In addition, it is desirable to provide a method for making these structures at the nanometer scale. These and other problems with the prior art processes and designs are obviated by the present invention. The references cited in this application infra and supra, are hereby incorporated in this application by reference. However, cited references or art are not admitted to be prior art to this application.

SUMMARY OF THE INVENTION

The invention provides an apparatus and method for nanopore construction. The apparatus comprises a rigid frame supporting a tensile diaphragm, wherein the tensile diaphragm has an insert portion of a dissimilar material that may be in compression. The tensile diaphragm may comprise a silicon nitride material. The tensile diaphragm has a length to thickness ratio from about 4 to about 1000, with a typical value of 250.

The invention also provides a method of making the apparatus. The method of making the apparatus comprises providing a composite tensile diaphragm supported on a rigid frame, the tensile diaphragm having a first tensile layer in contact with a second layer susceptible to selective etching in an etchant which etches neither the first tensile layer nor the desired dissimilar material, defining a photoresist layer on the exposed surface of the first tensile layer, selectively removing photoresist to expose a region of the tensile layer, removing the exposed region of the tensile layer to expose a region of the second layer, depositing a layer of dissimilar material on both the first tensile layer and the exposed region of the second layer, optionally selectively removing a region of the dissimilar material, and removing the exposed region of the second layer by etching from the side of the diaphragm opposite the tensile layer, thus exposing a lower surface of the region comprising the dissimilar material. A nanopore may then be fabricated in the region comprising the dissimilar material.

BRIEF DESCRIPTION OF THE FIGURES

The invention is described in detail below with reference to the following figures.

DETAILED DESCRIPTION OF THE INVENTION

Figure 1:
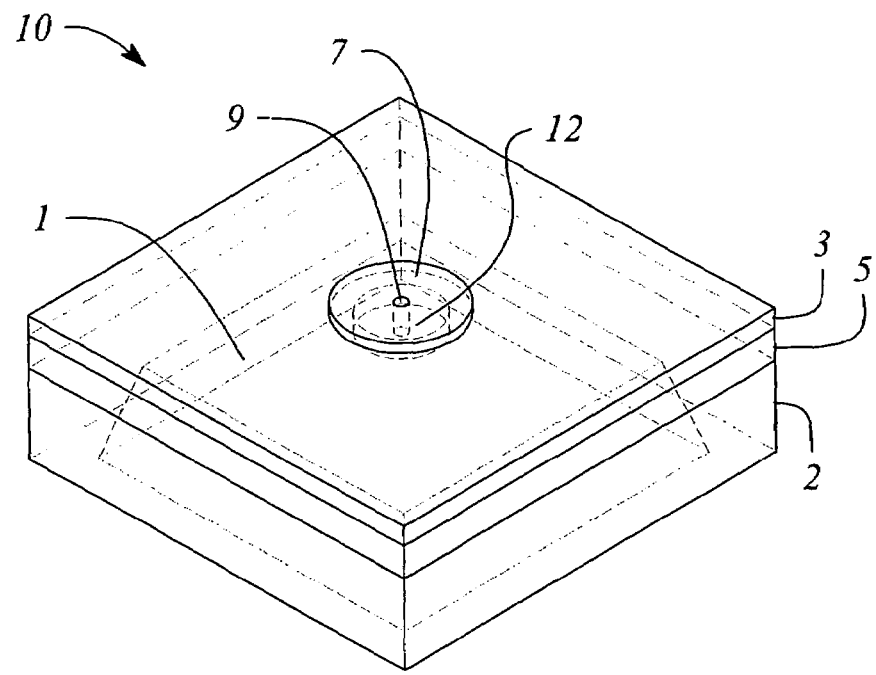
FIG. 1 shows a schematic representation of the structure of the present invention.

Before describing the present invention in detail, it is to be understood that this invention is not limited to specific compositions, method steps, or equipment, as such may vary. It is also to be understood that the terminology used herein is for the purpose of describing particular embodiments only, and is not intended to be limiting. Methods recited herein may be carried out in any order of the recited events that is logically possible, as well as the recited order of events.

Unless defined otherwise below, all technical and scientific terms used herein have the same meaning as commonly understood by one of ordinary skill in the art to which this invention belongs. Still, certain elements are defined herein for the sake of clarity. In the event that terms in this application are in conflict with the usage of ordinary skill in the art, the usage herein shall be controlling.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Methods recited herein may be carried out in any order of the recited events that is logically possible, as well as the recited order of events.

It must be noted that, as used in this specification and the appended claims, the singular forms "a", "an" and "the" include plural referents unless the context clearly dictates otherwise.

The term "about" refers to being closely or approximate to, but not exactly. A small margin of error is present. This margin of error would not exceed plus or minus the same integer value. For instance, about 0.1 micrometers would mean no lower than 0 but no higher than 0.2.

The term "nanopore" refers to any pore or hole between at least a pair of electrodes or a hole in a solid substrate. Nanopores can range in size and can range from about 1 nm to about 300 nm. Most effective nanopores have been roughly around 2 nm.

The term "adjacent" refers to anything that is near, next to or adjoining. For instance, a tensile layer may be near a compressive layer, next to a compressive layer or adjoining a compressive layer.

The term "substantially flat" refers to material that is nearly flat or planar in design. The material or layer may be under tension and contain one or more small wrinkles. The material in most cases would show absence of substantial wrinkles or buckling. In most cases, this term should be interpreted to be nearly or approximately uniformly flat. There are limited or no uneven surfaces.

The term "lateral extent" refers to a direction or directions lying substantially parallel to the substantially flat major surfaces of a component of a diaphragm, diaphragm component, or entire device. Thus, for example, a long thin finger of material meandering along a surface has a lateral extent that is small in relation to its overall length in a direction perpendicular to that length, and a lateral extent that is long in the direction of its length. Again, for example, an area of circular shape has a lateral extent that is uniform in all directions parallel to the major surface in which it lies.

The term "tensile diaphragm" refers to a diaphragm which has one of a purely tensile local strain energy and a local strain energy which has both tensile and compressive components which, when integrated through the thickness of the diaphragm in a small area of the diaphragm, evaluates to a local net strain energy which is tensile. The term "tensile diaphragm" also refers to a diaphragm that has a net tensile strain energy when the local strain energy is integrated over the entire surface area of the diaphragm, including any areas which may have a purely compressive strain energy.

Figure 2:
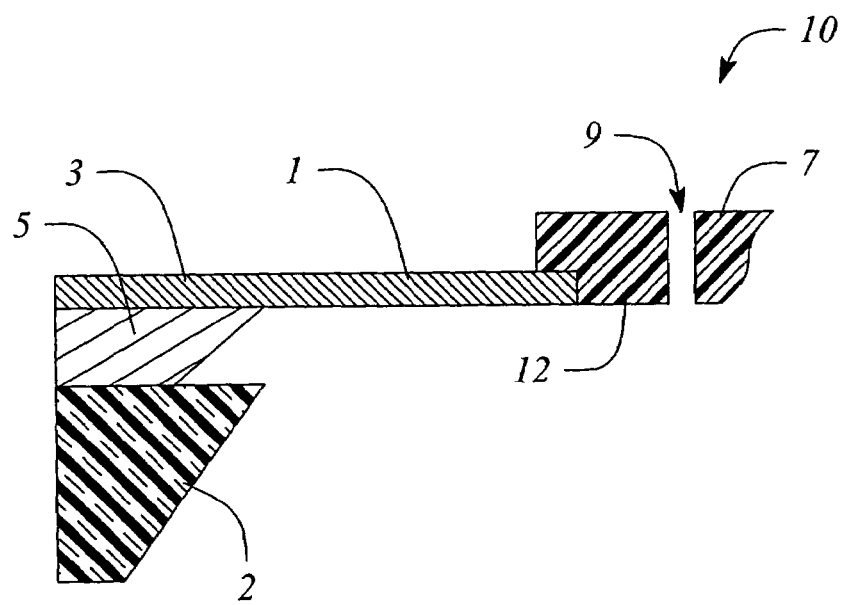
FIG. 2 shows a cross-sectional view of the structure of of the present invention.

FIGS. 1–2 show the apparatus 10 of the present invention. The figures are not drawn to scale. A rigid frame 2 supporting a tensile diaphragm 1 is generally illustrated in the figures. The diaphragm may range in lateral dimensions from 5 to at least 100 micrometers. Etchable layer 5 beneath diaphragm 1 supports the edges of the diaphragm 1 and is absent from a region beneath the diaphragm, and is also absent from a region beneath insert 7 of dissimilar material. Insert 7 is supported by diaphragm 1, but extends through diaphragm 1 in a region 12 which may vary in lateral extent from about 50 nm to about 60 micrometers. A nanopore 9 fabricated within the structure of the present invention is shown by way of example extending through insert 7. The dimensions described here are for illustrative purposes only and should not be interpreted to limit the scope of invention.

The insert region 7 and layer 11 may comprise any of a number of different materials known in the art, or a combination of materials. Such materials include polymers including but not limited to polyimides, photoresists, and Parylene®. Other materials include but are not limited to monolayers and multiple layers of various molecules, metals, and insulators. Methods of deposition suitable for forming the material in region 7 include but are not limited to spincasting, sputtering, evaporation, UV polymerization, thermal polymerization, catalyzed polymerization, low-pressure polymerization, chemical vapor deposition, ion beam deposition, plasma deposition, atomic layer deposition, vacuum self-assembly, low-pressure self-assembly, and aqueous self-assembly.

For instance, the insert 7 may comprise polyimide. Polyimide precursors are available from, for example, DuPont in liquid form that can be spun onto a silicon wafer comprising many instances of the present invention. The liquid is then dried to form a thin film, and thermally reacted in a process of "imidization" to form the final polyimide film. The polyimide film may be photolithographically defined by various techniques well known to those in the semiconductor industry.

Having described the apparatus of the invention, a description of the method is now in order.

In general, the method of making a tensile diaphragm with an insert comprises providing a composite diaphragm comprising an upper layer of an upper material and a lower layer of a lower material supported on a rigid frame, defining a region to be etched on top of the diaphragm, etching away a region of the upper material to expose a region of the lower material, forming a layer of a material dissimilar to the upper material on the upper surface of the upper material and on the exposed region of the lower material, optionally defining a limited area of the dissimilar material on the diaphragm, and etching away the lower material from the lower surface of the diaphragm to expose a lower surface of the dissimilar material. A nanopore may then be fabricated in the dissimilar material.

Referring now to FIGS. 3A–3F, FIG. 3A shows a cross sectional view of the diaphragm 1 comprising a lower layer 5 of a lower material and an upper layer 3 of an upper material. Diaphragm 1 may be made or produced by techniques well known in the art, such as for example by depositing layers of silicon dioxide followed by silicon nitride on one surface of a silicon wafer and etching an opposing surface of the silicon wafer to remove a selected region of silicon and leave a diaphragm supported by a silicon frame 2 as noted in FIGS. 1 and 2. It is well known that if such etching is carried out, for example, in an aqueous solution of tetramethyl ammonium hydroxide, neither silicon nitride nor silicon dioxide are appreciably etched while the silicon is removed. Material combinations other than silicon dioxide and silicon nitride may also be employed, and many such materials are known in the semiconductor industry and elsewhere.

Figure 3A:
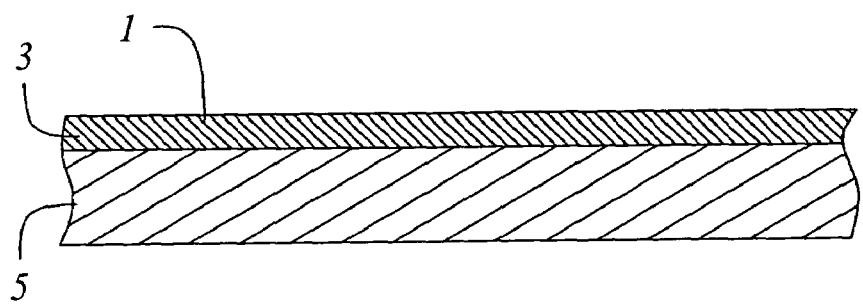
FIG. 3A shows a first step of the method of the present invention.
Figure 3B:
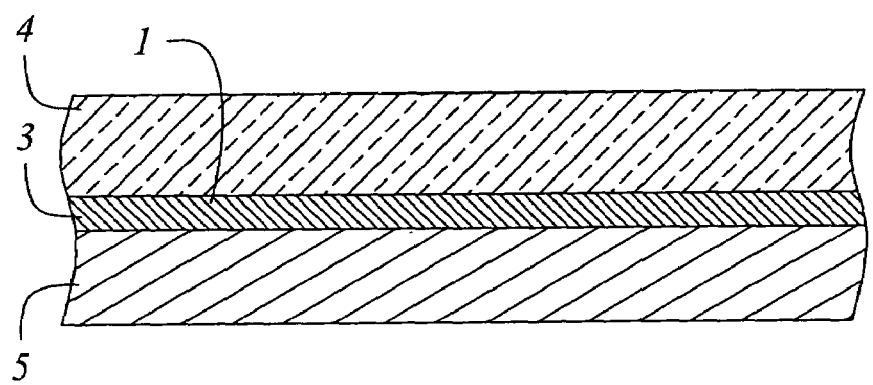
FIG. 3B shows a second step of the method of the present invention.
Figure 3C:
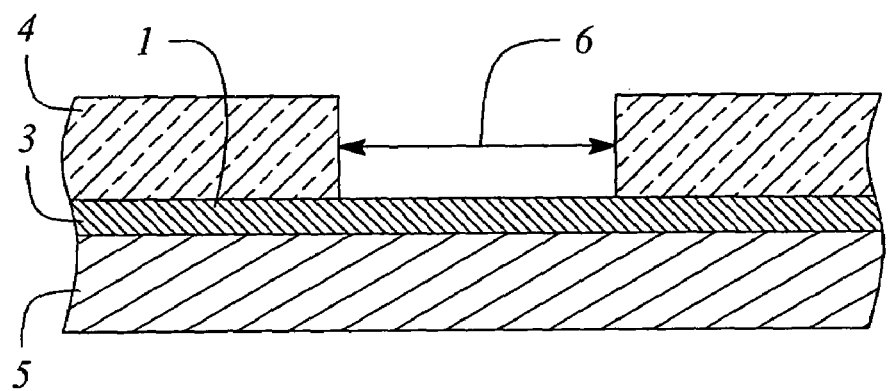
FIG. 3C shows a third step of the method of the present invention.

FIG. 3B shows a layer 4 of photoresist deposited on the top surface of the tensile diaphragm 1. FIG. 3C shows the use of photolithography or a similar technique to define a region 6 in the photoresist layer 4, which region 6 is then etched away to expose a region of layer 3. Region 6 may vary in shape and diameter, but is likely to be circular and around 5 micrometers in diameter.

Figure 3D:
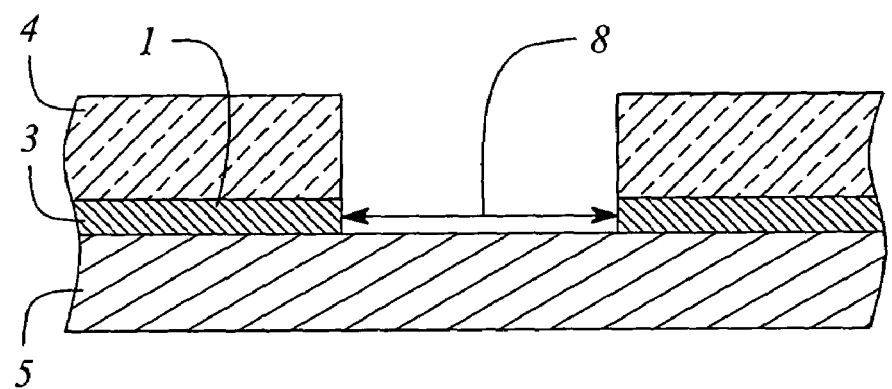
FIG. 3D shows a fourth step of the method of the present invention.

FIG. 3D shows the next step of the present invention. Plasma etching is used to etch through region 8 of layer 3, until the layer 5 is reached. Typically layer 3 comprises silicon nitride and layer 5 comprises silicon dioxide. It is well known in the art that there are techniques available which maximize the etch rate of silicon nitride in relation to silicon dioxide during plasma etching. See, for example, the description of a 40:1 etch rate selectivity of silicon nitride to silicon dioxide in "High-Selectivity Silicon Nitride Etch Process," by Ying Wang, et. al., Semiconductor International, Jul. 1, 1998, available on the internet at http://www.reed-electronics.com/semiconductor/index.asp? layout= article&articleid=CA163999&rid=0&rme=0&cfd=1. Thus, for a typical silicon nitride layer thickness of 200 nm, and a typical silicon dioxide layer thickness of 500 nm, it is possible to completely remove a region of the silicon nitride layer while minimally etching either the upper surface of the silicon dioxide layer or the exposed lower surface of the silicon nitride layer. Optionally, the exposed lower surface of the silicon dioxide layer may be protected by a deposited region, not shown, of a material such as photoresist, but such protection is not necessary in most cases.

Figure 3E:
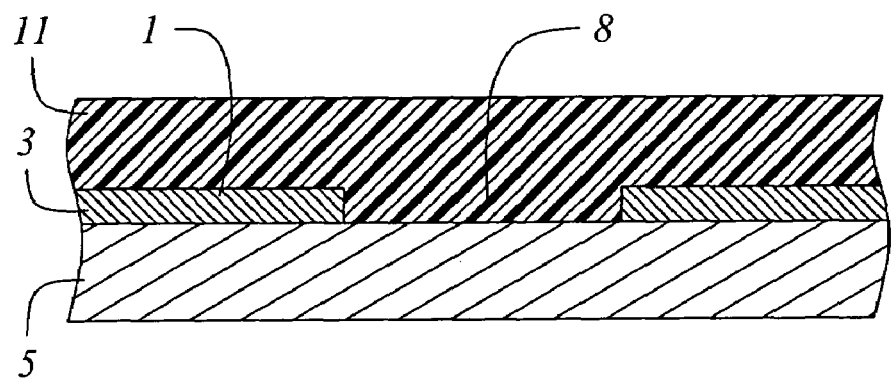
FIG. 3E shows a fifth step of the method of the present invention.
Figure 3F:
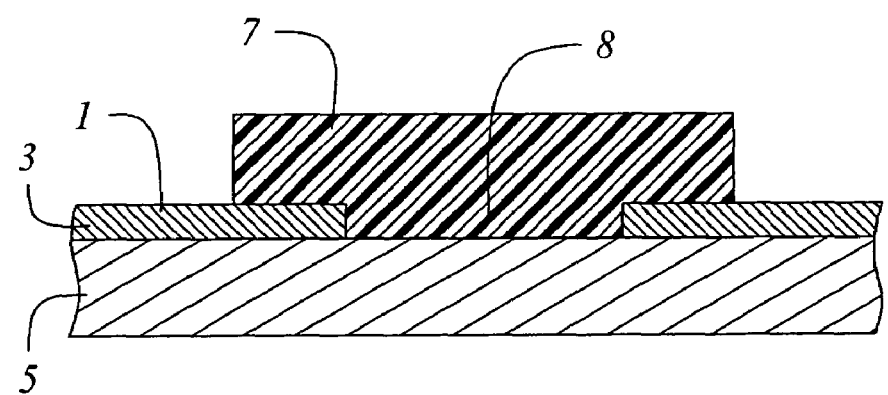
FIG. 3F shows a sixth step of the method of the present invention.

FIG. 3E shows a next step of the present invention. A layer 11 comprising a material dissimilar to both the upper layer 3 and the lower layer 5 is deposited onto the top surface of the diaphragm 1. In region 8, layer 11 contacts layer 5. Optionally, as shown in FIG. 3F, the lateral extents of layer 11 may be defined to form region 7.

Figure 3G:
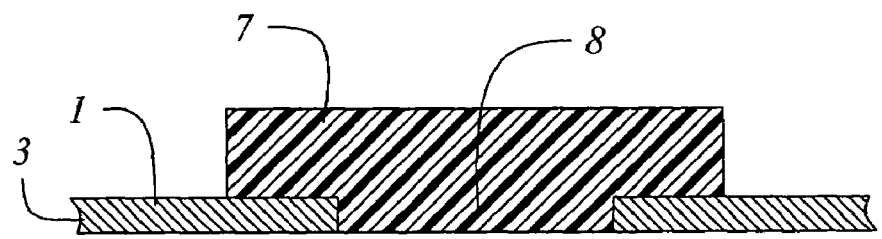
FIG. 3G shows a seventh step of the method of the present invention.

As shown in FIG. 3G, layer 5 is then etched away from the bottom surface of diaphragm 1, leaving region 7 of the dissimilar material supported in a diaphragm comprising layer 3. For this step, it is important to use an etchant for layer 5 that does not etch either the material of layer 3 or the material of region 7. For example, if layer 3 comprises silicon nitride and region 7 comprises polymide, while layer 5 comprises silicon dioxide, it is possible to use a hydrofluouric acid etchant to etch away layer 5 while leaving layer 3 and region 7. It is often important in such a case to use an adhesion promotion layer between the layer 11 layer and the diaphragm 1; such adhesion promotion layers are known to those skilled in the art, and their use is to be assumed when needed even though not explicitly shown in the fabrication process described herein. See, for example, "Wire bonds over active circuits," Heinen, G., et al., Electronic Components and Technology Conference, 1994. Proceedings. $44^{th}$, that paper describes the use of an aluminum chelate coupling agent with polyimide. The etching step shown in FIG. 3G completes the fabrication process for the present invention.

Figure 3H:
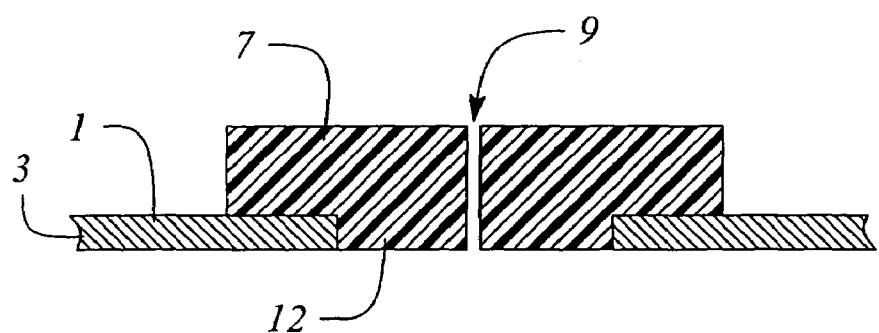
FIG. 3H shows an eighth step of the method of the present invention.

By way of example, FIG. 3H shows a nanopore fabricated through region 7, by using a focused ion beam to drill a hole through region 7 with a diameter on the order of 50–100 nm, followed by sculpting in a low energy ion beam to reduce the diameter of a portion of the hole to dimensions on the order 1–50 nm, forming nanopore 9.

It will be appreciated that the fabrication sequence described above is by way of example only, and that there are various techniques well known to those skilled in the art that may be used to arrive at the same final structure without departing from the scope and spirit of the present invention. For example, silicon nitride may be etched in hot phosphoric acid instead of in a plasma etch system, and various dry etching techniques may be employed instead of plasma etching. Shadow masking may be used instead of photolithography, and metal layers may be used instead of photoresist as etch-resistant layers. Instead of forming a diaphragm by etching completely through a silicon wafer, which is a technique called "bulk micromachining," various techniques for forming diaphragms on one surface of a substrate, collectively known as "surface micromachining" techniques, may be employed.

It will be appreciated that the fabrication of a nanopore in a region 7 may be accomplished by means other than focused ion beam drilling and argon ion beam sculpting. For example, other known means of fabricating a nanopore include masking with a nanoparticle followed by layer evaporation around the masking nanoporticle, next followed by removal of the nanoparticle and etching within the hole masked by the nanoparticle. Such techniques, both known and unknown, may be used to fabricate nanopores within the region 7 of the present invention.

It will be appreciated that, while the present invention is aimed toward utility in fabrication of nanopore structures, it may prove to have utility for fabrication of other devices both known and unknown. Such devices include those of microscale and nanoscale dimensions. Microscale dimensions are defined to include dimensions from 100 nm to 1 mm, and nanoscale dimensions are defined to include dimension from 0.1 nm to 1 um.

It will be appreciated that the description provided above has been for a case where the diaphragm completely surrounds the lateral extent of region 7. However, such complete surrounding is not a necessity of the present invention, and the lateral extent of region 7 may extend, in a sufficiently thin fashion or a sufficiently narrow fashion, or both, that buckling is avoided or diaphragm strength is not compromised, or both, to be coincident in one or more lateral directions with the lateral extent of the composite diaphragm 1. Accordingly, and in addition, narrow fingers of region 7 may extend in multiple fashions within the lateral area of diaphragm 1 without producing buckling of either region 7 or diaphragm 1. Additionally, multiple instances of region 7 may be present within the area of diaphragm 1. Additionally, polymer layer 11 may cover the entire area of the diaphragm 1 and may be contiguous with region 7.

It will be appreciated that having a tensile diaphragm in the structure of the present invention is preferred from the perspectives of mechanical stability and device robustness. However, the structure of the present invention may be fabricated with a diaphragm having a net compressive characteristic, as long as such compressive characteristic is not sufficiently large to destroy the functionality of the device.

I claim:

1. A structure for the construction of one of a microscale and nanoscale device, comprising
    a rigid frame supporting a diaphragm comprising a first material, the diaphragm having an opening therethrough,
    a region of a second material disposed in the opening and supported by the diaphragm,
    wherein the diaphragm is in tension, and wherein the first material and the second material are different.

2. A structure as recited in claim 1, wherein the diaphragm comprises a layer of a silicon nitride.

3. A structure as recited in claim 1, wherein the second material comprises one of polyimides, photoresists, paraxyfene, organic molecules, inorganic molecules, metal, and insulators.

4. A structure as recited in claim 1, wherein the second material comprises polyimide.

5. A structure as recited in claim 1, wherein the nanoscale device is nanopore.

6. A structure as recited in claim 2, wherein the silicon nitride layer is from 100 nm to 300 nm in thickness.

7. A structure as recited in claim 2, wherein the silicon nitride layer is about 200 nm thick.

8. A structure as recited in claim 1, wherein the width of the diaphragm is about 40 micometers.

9. A structure as recited in claim 1, wherein the opening has a diameter of about 5 micrometers.

10. A structure for the construction of one of a microscale and nanoscale device, comprising a rigid frame supporting a diaphragm comprising a first material, the diaphragm having an opening therethrough, a region of a second material disposed in the opening and supported by the diaphragm, wherein the second material comprises polyimide.

11. A structure as recited in claim 10, wherein the diaphragm comprises a layer of silicon nitride.

12. A structure as recited in claim 10, wherein the nanoscale device is nanopore.

13. A structure as recited in claim 11, wherein the silicon nitride layer is from 100 nm to 300 nm in thickness.

14. A structure as recited in claim 11, wherein the silicon nitride layer is about 200 nm thick.

15. A structure for the construction of one of a microscale and nanoscale device, comprising a rigid frame supporting a diaphragm comprising a first material, the diaphragm having an opening therethrough, a region of a second material disposed in the opening and supported by the diaphragm, wherein the opening has a diameter of about 5 micrometers.

16. A structure as recited in claim 15, wherein the diaphragm comprises a layer of a silicon nitride.

17. A structure as recited in claim 15, wherein the second material comprises one of polyimides, photoresists, paraxylene, organic molecules, inorganic molecules, metal, and insulators.

18. A structure as recited in claim 15, wherein the second material comprises polyimide.

19. A structure as recited in claim 15, wherein the nanoscale device is a nanopore.

20. A structure for the construction of one of a microscale and nanoscale device, comprising a rigid frame supporting a diaphragm comprising a first material, the diaphragm having an opening therethrough, a region of a second material disposed in the opening and supported by the diaphragm, wherein said region of a second material comprises a single nanopore, and wherein the first material and the second material are different.

21. A structure as recited in claim 1, wherein said diaphragm has a net tensile strain energy when the local strain energy is integrated over the entire surface area of the diaphragm.

22. A structure as recited in claim 1, wherein a lateral portion of said diaphragm does not contact said rigid frame.

23. A structure as recited in claim 20, wherein said diaphragm has a net tensile strain energy when the local strain energy is integrated over the entire surface area of the diaphragm.

24. A structure as recited in claim 20, wherein a lateral portion of said diaphragm does not contact said rigid frame.

* * * * *